(12) United States Patent
Saguchi et al.

(10) Patent No.: US 9,131,673 B2
(45) Date of Patent: Sep. 15, 2015

(54) SUSTAINED RELEASE PREPARATION COMPRISING A FOAMED CAPILLARY TUBE

(75) Inventors: Ryuichi Saguchi, Joetsu (JP); Kinya Ogawa, Tokyo (JP); Takehiko Fukumoto, Joetsu (JP); Tsugio Ogata, Shiki (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 1795 days.

(21) Appl. No.: 11/913,366

(22) PCT Filed: Apr. 11, 2007

(86) PCT No.: PCT/JP2007/057969
§ 371 (c)(1),
(2), (4) Date: Nov. 1, 2007

(87) PCT Pub. No.: WO2007/119744
PCT Pub. Date: Oct. 25, 2007

(65) Prior Publication Data
US 2008/0187597 A1 Aug. 7, 2008

(30) Foreign Application Priority Data

Apr. 11, 2006 (JP) .................... 2006-108536

(51) Int. Cl.
| | |
|---|---|
| *A01N 63/00* | (2006.01) |
| *A01P 17/00* | (2006.01) |
| *A01M 1/20* | (2006.01) |
| *A01N 25/18* | (2006.01) |
| *A01N 25/34* | (2006.01) |
| *A01M 1/02* | (2006.01) |
| *A01N 31/00* | (2006.01) |

(52) U.S. Cl.
CPC ............ *A01M 1/2044* (2013.01); *A01N 25/18* (2013.01); *A01N 25/34* (2013.01); *A01M 1/02* (2013.01); *A01N 31/00* (2013.01)

(58) Field of Classification Search
None
See application file for complete search history.

(56) References Cited

U.S. PATENT DOCUMENTS

| | | | |
|---|---|---|---|
| 4,600,146 A | 7/1986 | Ohno | |
| 4,605,165 A * | 8/1986 | Van Loveren et al. | ............ 239/6 |
| 6,065,687 A | 5/2000 | Suzuki et al. | |
| 6,216,960 B1 | 4/2001 | Aiba et al. | |

FOREIGN PATENT DOCUMENTS

| | | | |
|---|---|---|---|
| EP | 0 342 126 A2 | 5/1989 | |
| EP | 0 683 977 A1 | 11/1995 | |
| EP | 0 753 253 A1 | 1/1997 | |
| EP | 0 816 430 A2 | 1/1998 | |
| EP | 0913088 * | 5/1999 | ............ A01M 1/20 |
| EP | 0683977 * | 8/2000 | ............ A01M 1/20 |
| EP | 1 459 626 A1 | 9/2004 | |
| JP | 57-156403 A | 9/1982 | |
| JP | 62-145001 A | 6/1987 | |
| JP | 62-198201 U | 12/1987 | |
| JP | 3-255003 A | 11/1991 | |
| JP | 7-148812 A | 6/1995 | |
| JP | 7-313035 A | 12/1995 | |
| JP | 8-322447 A | 12/1996 | |
| JP | 11-225646 A | 8/1999 | |

OTHER PUBLICATIONS

International Search Report for PCT/JP2007/057969.
Supplementary European Search Report for Application No. EP 07 74 1405, Dated October 28, 2010.

* cited by examiner

*Primary Examiner* — Thane Underdahl
(74) *Attorney, Agent, or Firm* — Roberts Mlotkowski Safran & Cole, P.C.; David S. Safran

(57) ABSTRACT

Provided is a sustained release preparation capable of uniformly releasing therefrom a volatile chemical for a long period of time even if the amount of a liquid chemical remaining in a tubular container of the sustained release preparation becomes small. Also provided is a container for sustained release preparation, the container being tubular and comprising two layers of outer and inner layers, the inner layer having a thickness of 0.12 to 1.2 mm and having a foamed structure permitting the soaking-up of a liquid chemical to a height of at least 25 mm by capillarity. Also provided is a container unit for sustained release preparation, the unit comprising two or more of the container combined.

10 Claims, 11 Drawing Sheets

SUSTAINED RELEASE PREPARATION COMPRISING A FOAMED CAPILLARY TUBE

TECHNICAL FIELD

The present invention relates to a sustained release preparation which can release a volatile chemical such as a sex pheromone, repellent or insecticide while keeping its concentration constant in an atmosphere, particularly to a sustained release preparation effective for controlling the emergence of insects by a sex pheromone released therefrom.

BACKGROUND ART

In the mating disruption for controlling the emergence density of insects through release of, for example, a sex pheromone at a constant concentration for a long period of time, it is required to gradually release a volatile chemical to ensure a long lasting effect thereof. The mating disruption means a method for disturbing mating of the insects by emitting a sex pheromone in fields at a concentration substantially higher than that released by insects so as to lower the communication ability of the insects such as an ability of male or female insects to recognize the individual opposite sex or to confirm the positions thereof. For the mating disruption, a sustained release preparation containing a sex pheromone of a insect is used.

The sustained release preparation has already been industrialized and commercially available. A sustained release preparation having a sex pheromone filled in a plastic capillary tube has become the mainstream owing to high stability of its performance (Patent Document 1).

However, the plastic capillary tube has a problem that a decrease in the amount of a liquid remaining in the tube as a result of release may lead to a reduction in the release area and thus a reduction in the release amount in the latter half of the release. With a view to overcoming the above-described problem, there has been proposed a plastic container comprising an porous inner layer which has pores communicated to each other and an outer layer having a similar quality to the inner layer (Patent Document 2).

Patent Document 1: Japanese Patent Application Unexamined Publication No. 57-156403/1982
Patent Document 2: Japanese Patent Application Unexamined Publication No. 7-313035/1995

DISCLOSURE OF THE INVENTION

Problem to be Solved by the Invention

The present inventors have found that even if a container has a porous inner layer having pores communicated to each other, it cannot always accomplish uniform release because of a difference in the wetting degree of the inner surface of the container. Accordingly, an object of the present invention is to provide a sustained release preparation capable of releasing a volatile chemical uniformly for a long period of time even if the amount of the liquid chemical remaining in a tubular container of the sustained release preparation becomes small.

Means for Solving the Problem

As a result of intensive investigation with a view to achieving the above-described object, it has been found that a container for a sustained release preparation, the container being tubular and comprising an inner layer having a foamed structure permitting the soaking-up, by capillary action, of a liquid chemical to a height exceeding 25 mm, and the inner layer having a thickness of 0.12 to 1.2 mm, is useful for overcoming the above-described problem, leading to the completion of the present invention.

More specifically, there is provided a container for a sustained release preparation, the container being tubular and comprising two layers, that is, an outer layer and an inner layer, wherein the inner layer has a thickness of 0.12 to 1.2 mm and has a foamed structure permitting the soaking-up, by capillary action, of a liquid chemical to a height exceeding 25 mm. There is also provided a container unit for a sustained release preparation comprising two or more of the above-described container. There is also provided a sustained release preparation comprising the container or the container unit; and a liquid chemical loaded inside of the container or the container unit. There is also provided a method for producing a container unit for a sustained release preparation by extrusion, the unit comprising at least two tubular containers each having two layers of outer and inner layers, the inner layer having a thickness from 0.12 to 1.2 mm, the method comprising a step of simultaneously extruding an inner layer-forming polymer and an outer layer-forming polymer by using dies which allows flow paths of the inner layer-forming polymer to be covered with a flow path or paths of the outer layer-forming polymer.

Effect of the Invention

According to the present invention, provided is a sustained release preparation capable of uniformly releasing a volatile chemical for a long period of time even if an amount of a liquid chemical remaining in a tubular container of the sustained release preparation becomes small.

BEST MODE FOR CARRYING OUT THE INVENTION

The present invention can provide a sustained release preparation comprising a tubular container comprising two layers which are outer and inner layers, the inner layer having a thickness of 0.12 to 1.2 mm and having a foamed structure permitting the soaking-up of a liquid chemical to a height exceeding 25 mm by capillarity; and the liquid chemical placed in the tubular container.

The container for a sustained release preparation according to the present invention is tubular and the inner layer has a foamed structure permitting the soaking-up of a liquid chemical to a height exceeding 25 mm by capillarity and has a thickness of 0.12 to 1.2 mm.

Whether or not a capillary tube (an inner layer) has a foamed structure permitting the soaking-up of a liquid chemical to a height exceeding 25 mm by capillarity can be determined as shown in FIG. 1 by studying whether or not a capillary tube 11 can soak up a colored liquid chemical 12 to a predetermined height when one end of the tube 11 is dipped in the liquid chemical 12.

More specifically, a capillary tube (inner layer) 11 to be used for a sustained release preparation is inserted at room temperature (25° C.) into a bottle 101 having a diameter of 3 cm and height of 6 cm and containing a liquid chemical 12 filled to a height of 1 cm from the bottom wherein the chemical is to be used for the sustained release preparation. The capillary tube is inserted into the liquid chemical to a depth of 5 mm from the liquid surface thereof. The capillary tube is fixed vertically via a wire 102. After the bottle is left as it is for 24 hours while preventing evaporation of the liquid chemical from the bottle, a difference between the liquid surface in the bottle and the liquid surface in the capillary tube is defined as a soaking-up height. The capillary tube having a soaking-up height exceeding 25 mm can be used as the inner layer.

The capillary tube (inner layer) 11 to be used for a sustained release preparation may be a capillary tube of only an inner layer without an outer layer, or a capillary tube comprising both inner and outer layers. The capillary tube may be not limited to the capillary tube to be used for a sustained release preparation but in any form which can have a correlation with the capillary tube to be used for a sustained release preparation so that soak-up of a liquid chemical to a height exceeding 25 mm by capillarity upon use can be confirmed. As the liquid chemical, a liquid chemical to be used for a sustained release preparation may be preferred, but another liquid chemical having correlation with the liquid chemical to be used for a sustained release preparation may be also usable.

It is known that an increasing height (h) of a liquid by capillarity is given by the following equation:

$$h = 2\gamma \cos \theta / r\rho g \qquad (1)$$

wherein γ means surface tension of the liquid, θ means a contact angle, r means a tube radius, ρ means a liquid density, and g means acceleration due to gravity. As can be understood from the equation (1), h only depends on r when the liquid and material are determined. In the case of a foamed structure, r is not always fixed but generally has some distribution. Hence, any capillary tube having a foamed structure is not always suited as a sustained release preparation.

According to the present invention, the sustained release preparation is selected so that the measured soak-up height is more than 25 mm, preferably 30 mm or greater when a capillary tube having a foamed structure is soaked in a liquid chemical to be used for a sustained release preparation. When the height is not greater than 25 mm, wetting of the tube with the liquid is insufficient so that uniform release cannot be accomplished.

The thickness of the inner layer of the tubular container having a foamed structure is from 0.12 to 1.2 mm, preferably from 0.2 to 1.0 mm. When the thickness of the inner layer is less than 0.12 mm, a penetration and retention amount of liquid chemical is insufficient so that uniform release cannot be accomplished. In particular, in the case of a container having a large inner diameter to fill a larger amount of liquid chemical therein, uniform release cannot be accomplished. When the thickness exceeds 1.2 mm, an adsorption amount of liquid chemical to a polymer forming a foamed layer increases, leading to an increase in an amount of liquid chemical which has remained unreleased.

The inner layer of the tubular container has a cell diameter range of preferably from 0.2 to 700 μm, more preferably from 0.3 to 500 μm. With regards to the cell diameter distribution, cells having a diameter from 0.2 to 100 μm accounts for 50 to 95% (number average) and cells having a diameter of 100 to 700 μm accounts for 5 to 50% (number average). The cell diameter can be determined by observing the structure of the tubular container through a microscope and measuring pore sizes.

As shown in FIG. 2, portion A having a smaller cell diameter serves to soak up a liquid far from the liquid surface, while portion B having a larger cell diameter serves to retain a large amount of the liquid. This is presumed to cause a large increase in the height of the liquid. On the other hand, in a capillary tube whose soaking-up height does not exceed 20 mm, pores have uniform diameters even if the capillary tube is porous and their pores are connected to each other as shown in FIG. 3.

The container for a sustained release preparation according to the present invention may be a tubular container as shown in FIG. 4 obtained by covering a first layer (inner layer) having a foamed structure with a second layer (outer layer) C of a polymer for controlling the penetration rate of a liquid chemical. Preferred examples of the polymer for controlling the penetration rate of a liquid chemical may include polyolefins, olefin copolymers (such as olefin-olefin copolymers and olefin-ester copolymers), aliphatic polyesters, and aliphatic ester copolymers (such as aliphatic ester-aliphatic ester copolymers). Specific examples may include high density polyethylene, polypropylene, ethylene-vinyl acetate copolymer, blend polymer of ethylene-vinyl acetate copolymer and aliphatic polyester, aliphatic polyester (biodegradable polymer), copolymer (biodegradable polymer) of butylene succinate and butylene adipate, and copolymer (biodegradable polymer) of butylene succinate and ethylene terephthalate.

A covering layer (outer layer) for controlling the penetration of a liquid chemical controls a dissolution or diffusion rate of the liquid chemical in or to the covering polymer or an evaporation rate of the liquid chemical from the outer surface. Accordingly, the liquid chemical and the polymer have adequate compatibility.

Since the thickness of the outer layer greatly influences the penetration rate of a liquid chemical, an adequate thickness has to be selected. Although no particular limitation is imposed on the size of the tubular container, it may have a preferable inner diameter of 0.5 to 3 mm and a preferable outer diameter of 1.5 to 8 mm from the viewpoints of its preparation and handling. The thickness of the outer layer may be preferably determined in consideration of the thickness of the inner layer so that the tubular container has a size within the above-described range. The tubular container has a length of preferably from 50 to 2,000 mm, more preferably from 100 to 400 mm.

The inner layer of the tubular container of the sustained release preparation according to the present invention may be obtained by molding a polymer containing an blowing agent at a decomposition temperature of the blowing agent or higher.

Although no particular limitation is imposed on the polymer to which the blowing agent is added, preferred examples may include high density polyethylene, low density polyethylene, crosslinked polyethylene, ethylene-vinyl acetate copolymer, aliphatic polyester, blend polymer of polyolefin and aliphatic polyester, and polylactic acid.

The blowing agent may include organic blowing agents such as azodicarbonamide and p,p'-oxybisbenzene sulfonyl hydrazide, and inorganic blowing agents such as sodium bicarbonate. Since the foaming degree varies greatly depending on the concentration or processing temperature of the blowing agent, the concentration and processing temperature of the blowing agent have to be examined to obtain a desirably foamed capillary tube.

A foamed structure permitting soaking-up of a liquid chemical to a height exceeding 25 mm by capillarity can be obtained by adjusting a foaming ratio preferably to 15% by volume or greater, more preferably 40% by volume or greater.

Specific examples of the foamed structure may include that obtained by foaming low density polyethylene containing 2% by weight of azodicarbonamide at 190 to 200° C. and by foaming polylactic acid containing 2.4% by weight of p,p'-oxybisbenzene sulfonyl hydrazide at 160 to 170° C.

The inner layer can be also produced by adding a blowing agent to an inner layer polymer which a filler has been added.

Examples of the filler may include talc, silica powder, titanium oxide, carbon black, magnesium silicate, calcium carbonate, magnesium carbonate, barium sulfate, aluminum sulfate and calcium sulfate. When the filler is used, air bubbles can be dispersed densely and an inner layer having a large cell diameter distribution ranging from 0.2 to 100 µm can be obtained.

The filler may be added preferably in an amount of from 4 to 60 parts by weight based on 100 parts by weight of the inner layer polymer. The amount may be particularly preferably from 10 to 50 parts by weight in view of the cell diameter distribution and strength of the inner layer.

For the formation of the inner layer, 1 to 5 parts by weight of silica powder may be preferably added to 100 parts by weight of the inner layer polymer. Addition of a silica powder can reduce the foaming temperature and form a foamed inner layer having air bubbles densely dispersed therein.

It may be preferable to use the silica powder having an average particle size of 7 to 40 µm and having a surface hydrophobized with a methyl group, a trimethylsilyl group, dimethylsilicone oil, octyl silane or the like. Specific examples may include "Aerosil R972", "Aerosil 200", "Aerosil R202", "Aerosil R805", "Aerosil R812", "Aerosil RX200" and "Aerosil RY200" (each produced by Toshin Chemicals Co., Ltd.), and "SS-30P", "SS-70", and "SS-50" (each produced by Tosoh Silica Corporation).

The container for a sustained release preparation according to the present invention being tubular and comprising a foamed layer therein may be produced preferably by extrusion. It may be produced more preferably by extruding a molten polymer for forming an outer layer through a die while allowing the foamed capillary tube to pass through a mandrel at the center of the die.

Alternatively, two extruders are provided, a foaming resin is inserted and extruded with one extruder so as to form a foamed capillary tube, while an outer layer-forming polymer for controlling the penetration rate of a liquid chemical is inserted and extruded with the other extruder so as to cover the outside of the foamed capillary tube.

Further alternatively, a container unit for a sustained release preparation having two or more of the tubular container combined can be produced by extruding an inner layer-forming polymer and an outer layer-forming polymer simultaneously by using dies which allow flow paths of the inner layer-forming polymer to be covered with a flow path or paths of the outer layer-forming polymer.

For example, when an inner layer-forming polymer and an outer layer-forming polymer are extruded simultaneously by using two extruders with dies having shapes capable of forming two or more tubes by extrusion, the inner layers of the tubes are inevitably bonded to each other. To solve the problem, as shown in FIG. 5, dies having such shapes which allows each flow path F1 of an inner layer-forming polymer to be covered with a flow path or paths F2 of an outer layer-forming polymer, wherein flow path has been divided into each flow path F1 for forming two or more tubes by extrusion.

The capillary tube thus obtained is filled with a liquid chemical, then sealed at both ends thereof and can be used as a sustained release preparation having the liquid chemical filled in a tubular container. A sustained release preparation having two or more of the tubular container combined may be used. Such a type of preparation can be used for a plurality of purposes by filling different liquid chemicals in the tubular containers, respectively. For example, FIG. 6(a) illustrates a sustained release preparation 20 having plastic capillary tubes (tubular containers) 22a and 22b combined via fusion connection ends 23. The tubular containers 22a and 22b can be separated if necessary as illustrated in FIG. 6(B).

A sustained release preparation in the circular form, obtained by separating the tubular containers combined, can be suspended easily and improve the working efficiency greatly, especially when used for the purpose of releasing a sex pheromone to reduce emergency of insects.

The liquid chemical may include a volatile liquid such as a sex pheromone, repellent or insecticide. Particularly, a sex pheromone is effective in a sustained release preparation for controlling the emergency of insects by releasing the sex pheromone.

The liquid chemical can be diluted with a solvent. In this case, the diluted chemical has to be soaked up to a height exceeding 25 mm by capillarity.

EXAMPLES

The present invention will hereinafter be described by Examples specifically. However, it should not be construed that the present invention is limited to or by these Examples.

Example 1

High density polyethylene to which 1 part by weight of sodium bicarbonate had been added as a blowing agent was extruded at 190° C. to produce a foamed capillary tube having an inner diameter of 1.22 mm and a thickness of 0.40 mm. A cross-sectional enlarged photograph of the capillary tube is shown in FIG. 7. The diameters of cells thus formed were measured and the distribution of the diameters of cells was determined based on cross-sectional enlarged photographs. The cells having diameters of 0.2 to 100 µm accounted for 73% (number average) and the cells having diameters of 100 to 700 µm accounted for 27% (number average).

The capillary tube was cut into a piece of 150 mm and dipped, at one end thereof, in a solution of Z8-dodecenyl acetate, which is a sex pheromone of the oriental fruit moth, wherein the solution had been stained red. The resulting tube piece was left as it was for 24 hours and then checked. As a result, the tube piece was stained red along the entire length thereof, indicating that the solution was soaked up to a height of 150 mm by capillarity.

Next, the foamed capillary tube was covered, on the outside thereof, with high density polyethylene by extrusion so as to form a covering layer (outer layer) having a thickness of 0.50 mm. A cross-sectional enlarged photograph of the capillary tube is shown in FIG. 4. The tube was filled with Z8-dodecenyl acetate, which is a sex pheromone of the oriental fruit moth. The tube was welded and cut so as to have a length of 200 mm, whereby a sustained release preparation having 240 mg of the sex pheromone enclosed was prepared.

The resulting preparation was exposed to predetermined conditions of a temperature of 30° C. and a wind speed of 0.7 m/s. The correlation between the released amount of sex pheromone and the elapsed time is shown in FIG. 8. It is evident in FIG. 8 that the preparation released the sex pheromone uniformly over 40 days. The remaining amount of the sex pheromone after 40 days' exposure corresponded to 10% of the initially filled amount.

Example 2

The foamed capillary tube obtained by extrusion in Example 1 was cut into a piece of 150 mm and dipped, at one end thereof, in a solution of Z11-tetradecenyl acetate, which is a sex pheromone of the oriental tea tortrix, wherein the solution had been stained red. The resulting tube piece was left as it was for 24 hours and then checked. As a result, the solution was soaked up to a height of 125 mm from the surface of the solution.

Next, the foamed capillary tube was covered, on the outside thereof, with high density polyethylene by extrusion so as to form a covering layer (outer layer) having a thickness of 0.50 mm. A cross-sectional enlarged photograph of the capillary tube is shown in FIG. 4. The tube was filled with Z11-tetradecenyl acetate, which is a sex pheromone of the oriental tea tortrix. The tube was welded and cut so as to have a length of 200 mm, whereby a sustained release preparation having 240 mg of the sex pheromone enclosed was prepared.

The resulting preparation was exposed to predetermined conditions of a temperature of 30° C. and a wind speed of 0.7 m/s. The correlation between the release amount of sex pheromone and the elapsed time is shown in FIG. 9. It is evident in FIG. 9 that the preparation released the sex pheromone uniformly over 60 days. The remaining amount of the sex pheromone after 60 days' exposure corresponded to 15% of the initially filled amount.

Example 3

The foamed capillary tube obtained by extrusion in Example 1 was cut into a piece of 150 mm and dipped, at one end thereof, in a solution of Z13-icosen-10-one, which is a sex pheromone of the peach fruit borer, wherein the solution had been stained red. The resulting tube piece was left as it was for 24 hours and then checked. As a result, the solution was soaked up to a height of 95 mm from the surface of the solution.

Next, the foamed capillary tube was covered, on the outside thereof, with high density polyethylene by extrusion so as to form a covering layer (outer layer) having a thickness of 0.50 mm. A cross-sectional enlarged photograph of the capillary tube is shown in FIG. 4. The tube was filled with Z13-icosen-10-one, which is a sex pheromone of the peach fruit borer. The tube was welded and cut so as to have a length of 200 mm, whereby a sustained release preparation having 240 mg of the sex pheromone enclosed was prepared.

The resulting preparation was exposed to predetermined conditions of a temperature of 30° C. and a wind speed of 0.7 m/s. The correlation between the release amount of sex pheromone and the elapsed time is shown in FIG. 10. It is evident in FIG. 10 that the preparation released the sex pheromone uniformly over 120 days. The remaining amount of the sex pheromone after 120 days' exposure corresponded to 18% of the initially filled amount.

Example 4

Polylactic acid to which 2.4 parts by weight of p,p'-oxybisbenzene sulfonyl hydrazide had been added as a blowing agent was extruded at 168° C. to produce a foamed capillary tube having an inner diameter of 1.2 mm and a thickness of 0.30 mm. A cross-sectional enlarged photograph of the capillary tube is shown in FIG. 11.

The capillary tube was cut into a piece of 150 mm and dipped, at one end thereof, in a solution of Z8-dodecenyl acetate, which is a sex pheromone of the oriental fruit moth, wherein the solution had been stained red. The resulting tube piece was left as it was for 24 hours and then checked. As a result, the tube piece was stained red along the entire length thereof and the solution was soaked up to a height of 70 mm by capillarity.

Next, the foamed capillary tube was covered, on the outside thereof, with a copolymer of butylene succinate and butylene adipate (the copolymer having succinate:adipate weight ratio of 80:20) by extrusion so as to form a covering layer (outer layer) having a thickness of 0.25 mm. The resulting tube was filled with Z8-dodecenyl acetate, which is a sex pheromone of the oriental fruit moth. The tube was welded and cut so as to have a length of 200 mm, whereby a sustained release preparation having 180 mg of the sex pheromone enclosed was prepared.

The resulting preparation was exposed to predetermined conditions of a temperature of 30° C. and a wind speed of 0.7 m/s. The correlation between the release amount of sex pheromone and the elapsed time is shown in FIG. 12. It is evident in FIG. 12 that the preparation released the sex pheromone uniformly over 60 days. The remaining amount of the sex pheromone after 60 days' exposure corresponded to 15% of the initially filled amount.

Example 5

High density polyethylene to which 1.5 parts by weight of azodicarbonamide had been added as a blowing agent was extruded at 190° C. to produce a foamed capillary tube having an inner diameter of 1.52 mm and a thickness of 0.15 mm.

The capillary tube was cut into a piece of 150 mm and dipped, at one end thereof, in a solution of Z8-dodecenyl acetate, which is a sex pheromone of the oriental fruit moth, wherein the solution had been stained red. The resulting tube piece was left as it was for 24 hours and then checked. As a result, the tube piece was stained red along the entire length thereof, indicating that the solution was soaked up to a height of 150 mm by capillarity.

Next, the foamed capillary tube was covered, on the outside thereof, with high density polyethylene by extrusion so as to form a covering layer (outer layer) having a thickness of 0.60 mm. The resulting tube was filled with Z8-dodecenyl acetate, which is a sex pheromone of the oriental fruit moth. The tube was welded and cut so as to have a length of 200 mm, whereby a sustained release preparation having 280 mg of the sex pheromone enclosed was prepared.

The resulting preparation was exposed to predetermined conditions of a temperature of 30° C. and a wind speed of 0.7 m/s. The correlation between the release amount of sex pheromone and the elapsed time is shown in FIG. 13. It is evident in FIG. 13 that the preparation released the sex pheromone uniformly over 60 days. The remaining amount of the sex pheromone after 40 days' exposure corresponded to 10% of the initially filled amount.

Example 6

High density polyethylene to which 1.5 parts by weight of azodicarbonamide had been added as a blowing agent was extruded at 190° C. to produce a foamed capillary tube having an inner diameter of 1.52 mm and a thickness of 1.1 mm.

The capillary tube was cut into a piece of 150 mm and dipped, at one end thereof, in a solution of Z8-dodecenyl acetate, which is a sex pheromone of the oriental fruit moth, wherein the solution had been stained red. The resulting tube piece was left as it was for 24 hours and then checked. As a result, the tube piece was stained red along the entire length thereof and the solution was soaked up to a height of 130 mm by capillarity.

Next, the foamed capillary tube was covered, on the outside thereof, with high density polyethylene by extrusion so as to form a covering layer (outer layer) having a thickness of 0.60 mm. The resulting tube was filled with Z8-dodecenyl acetate, which is a sex pheromone of the oriental fruit moth. The tube was welded and cut so as to have a length of 200 mm, whereby a sustained release preparation having 280 mg of the sex pheromone enclosed was prepared.

The resulting preparation was exposed to predetermined conditions of a temperature of 30° C. and a wind speed of 0.7 m/s. The correlation between the release amount of sex pheromone and the elapsed time is shown in FIG. 13. It is evident in FIG. 13 that the preparation released the sex pheromone uniformly over 55 days. The remaining amount of the sex pheromone after 40 days' exposure corresponded to 15% of the initially filled amount.

Example 7

High density polyethylene to which 2.0 parts by weight of azodicarbonamide as a blowing agent and 35 parts by weight of talc as a filler had been added was extruded with a first extruder at 190° C. High density polyethylene was extruded with a second extruder at 190° C. Consequently, a capillary tube having, outside of a foamed layer having an inner diameter of 1.52 mm and a thickness of 1.1 mm, an outer covering layer having a thickness of 0.60 mm was obtained.

The capillary tube was cut into a piece of 150 mm and dipped, at one end thereof, in a solution of Z8-dodecenyl acetate, which is a sex pheromone of the oriental fruit moth, wherein the solution had been stained red. The resulting tube piece was left as it was for 24 hours and then checked. As a result, the tube piece was stained red along the entire length thereof and the solution was soaked up to a height of 130 mm by capillarity.

Next, the foamed capillary tube was cut in round slices and a cross-sectional enlarged photograph of the slice (FIG. 14) was taken. Diameters of the cells formed in the capillary tube were measured and their distribution was determined. According to the distribution thus determined, cells having a diameter of 0.2 to 100 μm accounted for 90% (number average) and cells having a diameter of 100 to 700 μm accounted for 10% (number average).

The tube was filled with Z8-dodecenyl acetate, which is a sex pheromone of the oriental fruit moth. The tube was welded and cut so as to have a length of 200 mm, whereby a sustained release preparation having 280 mg of the sex pheromone enclosed was prepared.

The resulting preparation was exposed to predetermined conditions of a temperature of 30° C. and a wind speed of 0.7 m/s. The correlation between the release amount of sex pheromone and the elapsed time was measured.

As a result, the preparation released the sex pheromone uniformly over about 60 days. The remaining amount of the sex pheromone after 60 days' exposure corresponded to 10% of the initially filled amount.

Example 8

A copolymer of butylene succinate and butylene adipate to which 2.0 parts by weight of sodium bicarbonate as a blowing agent and 35 parts by weight of talc as a filler had been added was extruded at 165° C. with a first extruder to produce two tubes, while simultaneously, a copolymer of butylene succinate and butylene adipate was extruded at 165° C. with a second extruder. Consequently a capillary tube having two parallel tubes, each tube having a foamed layer having an inner diameter of 1.42 mm and a thickness of 0.3 mm, was covered, on the outside of the parallel tubes, with an outer covering layer having a thickness of 0.60 mm.

The resulting capillary tube was cut into a piece of 150 mm and dipped, at one end thereof, in a 1:1 mixed solution of Z11-hexadecenyl acetate and Z11-hexadecenal, which are sex pheromones of the cabbage moth, wherein the solution had been stained red. The resulting tube piece was left as it was for 24 hours and then checked. As a result, the tube piece was stained red along the entire length thereof and the solution was soaked up to a height of 100 mm by capillarity.

The foamed capillary tube was then sliced in rounds and a cross-sectional enlarged photograph of the slice was taken (FIG. 15). Diameters of the cells thus formed were measured and their distribution was determined. According to the distribution thus determined, cells having a diameter of 0.2 to 100 μm accounted for 60% (number average) and cells having a diameter from 100 to 700 μm accounted for 40% (number average).

The tube was filled with a 1:1 mixed solution of Z11-hexadecenyl acetate and Z11-hexadecenal, which are sex pheromones of the cabbage moth. The tube was welded and cut so as to have a length of 200 mm, whereby a sustained release preparation having 460 mg of the sex pheromones enclosed was prepared.

The resulting preparation was exposed to predetermined conditions of a temperature of 30° C. and a speed of 0.7 m/s. The correlation between the release amount of sex pheromones and the elapsed time was measured.

As a result, the preparation released the sex pheromones uniformly over 60 days. The remaining amount of the sex pheromones after 60 days' exposure corresponded to 20% of the initially filled amount.

Example 9

High density polyethylene to which 2.0 parts by weight of azodicarbonamide as a blowing agent, 35 parts by weight of talc as a filler and 2.0 parts by weight of "R972" (product of Toshin Chemicals Co., Ltd.) as an aerogel had been added was extruded at 160° C. with a first extruder. High density polyethylene was extruded at 160° C. with a second extruder. Consequently, a capillary tube having, outside of the foamed layer having an inner diameter of 1.52 mm and a thickness of 1.1 mm, an outer covering layer having a thickness of 0.60 mm was obtained.

The resulting capillary tube was cut into a piece of 150 mm and dipped, at one end thereof, in a solution of Z8-dodecenyl acetate, which is a sex pheromone of the oriental fruit moth, wherein the solution had been stained red. The resulting tube piece was left as it was for 24 hours and then checked. As a result, the tube piece was stained red along the entire length thereof and the solution was soaked up to a height of 130 mm by capillarity.

The foamed capillary tube was then cut in round slice and a cross-sectional enlarged photograph (FIG. 16) of the slice was taken. Diameters of the cells thus formed were measured and distribution of the diameters of the cells was determined. According to the distribution thus determined, cells having a diameter from 0.2 to 100 μm accounted for 95% (number average) and cells having a diameter from 100 to 700 μm accounted for 5% (number average).

The tube was filled with Z8-dodecenyl acetate, which is a sex pheromone of the oriental fruit moth. The tube was welded and cut so as to have a length of 200 mm, whereby a sustained release preparation having 280 mg of the sex pheromone enclosed was prepared.

The resulting preparation was exposed to predetermined conditions of a temperature of 30° C. and a wind speed of 0.7 m/s. The correlation between the release amount of sex pheromone and the elapsed time was measured.

As a result, the preparation released the sex pheromone uniformly over about 60 days. The remaining amount of the sex pheromone after 60 days' exposure corresponded to 10% of the initially filled amount.

Comparative Example 1

High density polyethylene to which 1 part by weight of sodium bicarbonate as a blowing agent had been added was extruded at 155° C. to produce a foamed capillary tube having an inner diameter of 1.22 mm and a thickness of 0.40 mm. A cross-sectional enlarged photograph of the resulting capillary tube is shown in FIG. 3.

The capillary tube was cut into a piece of 150 mm and dipped, at one end thereof, in a solution of Z8-dodecenyl acetate, which is a sex pheromone of the oriental fruit moth, wherein the solution had been stained red. The resulting tube piece was left as it was for 24 hours and then checked. As a result, the solution was soaked up to a height of 25 mm from the surface of the solution.

Next, the foamed capillary tube was, on the outside thereof, covered with high density polyethylene by extrusion so as to form a covering layer (outer layer) having a thickness of 0.25 mm. The resulting tube was filled with Z8-dodecenyl acetate, which is a sex pheromone of the oriental fruit moth. The tube was welded and cut so as to have a length of 200 mm, whereby a sustained release preparation having 240 mg of the sex pheromone enclosed was prepared.

The resulting preparation was exposed to predetermined conditions of a temperature of 30° C. and a wind speed of 0.7 m/s. The correlation between the release amount of sex pheromone and the elapsed time is shown in FIG. 8. It is evident in FIG. 8 that the sustained release preparation released the sex pheromone uniformly over 30 days and then reduced its release rate gradually. The remaining amount of the sex pheromone after 30 days' exposure corresponded to 35% of the initially filled amount.

Comparative Example 2

High density polyethylene to which 1 part by weight of sodium bicarbonate as a blowing agent had been added was extruded at 190° C. to produce a foamed capillary tube having an inner diameter of 1.22 mm and a thickness of 0.10 mm.

The capillary tube was cut into a piece of 150 mm and dipped, at one end thereof, in a solution of Z8-dodecenyl acetate, which is a sex pheromone of the oriental fruit moth, wherein the solution had been stained red. The resulting tube piece was left as it was for 24 hours and then checked. As a result, the tube piece was stained red along the entire length thereof, indicating that the solution was soaked up to a height of 150 mm.

Next, the foamed capillary tube was covered, on the outside thereof, with high density polyethylene by extrusion so as to form a covering layer (outer layer) having a thickness of 0.50 mm. The resulting tube was filled with Z8-dodecadienyl acetate, which is a sex pheromone of the oriental fruit moth. The tube was welded and cut so as to have a length of 200 mm, whereby a sustained release preparation having 240 mg of the sex pheromone enclosed was prepared.

The resulting preparation was exposed to predetermined conditions of a temperature of 30° C. and a wind speed of 0.7 m/s. The correlation between the release amount of sex pheromone and the elapsed time is shown in FIG. 8. It is evident in FIG. 8 that the sustained release preparation uniformly released the sex pheromone over 40 days and then reduced the release rate gradually. The remaining amount of the sex pheromone after 40 days' exposure corresponded to 40% of the initially filled amount.

Comparative Example 3

High density polyethylene to which 1.5 parts by weight of azodicarbonamide as a blowing agent had been added was extruded at 190° C. to produce a foamed capillary tube having an inner diameter of 1.52 mm and a thickness of 1.3 mm.

The capillary tube was cut into a piece of 150 mm and dipped, at one end thereof, in a solution of Z8-dodecenyl acetate, which is a sex pheromone of the oriental fruit moth, wherein the solution had been stained red. The resulting tube piece was left as it was for 24 hours and then checked. As a result, the tube piece was stained red along the entire length thereof and the solution was soaked up to a height of 100 mm by capillarity.

Next, the foamed capillary tube was covered, on the outside thereof, with high density polyethylene by extrusion to form a covering layer (outer layer) having a thickness of 0.60 mm. The resulting tube was filled with Z8-dodecenyl acetate, which is a sex pheromone of the oriental fruit moth. The tube was welded and cut so as to have a length of 200 mm, whereby a sustained release preparation having 280 mg of the sex pheromones enclosed was prepared.

The resulting preparation was exposed to predetermined conditions of a temperature of 30° C. and a wind speed of 0.7 m/s. The correlation between the release amount of sex pheromone and the elapsed time is shown in FIG. 13. It is evident in FIG. 13 that the sustained release preparation released the sex pheromone uniformly over 40 days and then reduced the release rate drastically. The remaining amount of the sex pheromone after 40 days' exposure corresponded to 40% of the initially filled amount. It was found that most of the remaining sex pheromone had been dissolved in the polymer of the foamed layer of the tube.

BRIEF DESCRIPTION OF THE DRAWINGS

FIG. 6(A) illustrates a sustained release preparation having a combination of two capillary tubes (tubular containers), while FIG. 6(B) illustrates a sustained release preparation with two capillary tubes separated at the middle.

EXPLANATION OF SYMBOLS

Figure 1:
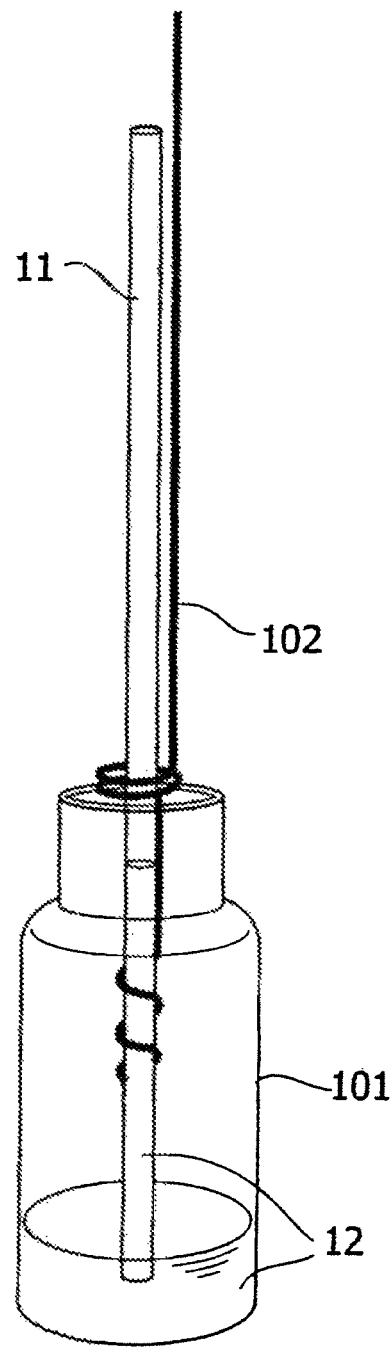
FIG. 1 illustrates a method for measuring a soaking-up height.
Figure 2:
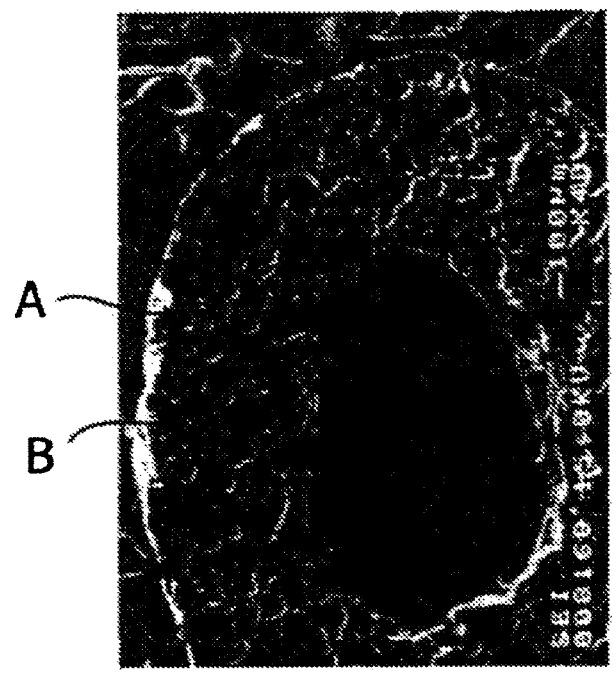
FIG. 2 exhibits a cross-sectional view (×40) of a foamed structure of the inner layer of a sustained release preparation.
Figure 3:
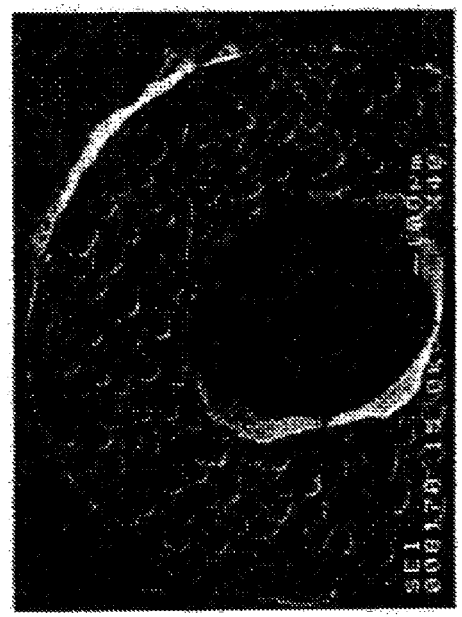
FIG. 3 exhibits a cross-sectional view (×40) of the foamed structure of a capillary tube having a soaking-up height of only 20 mm.
Figure 4:
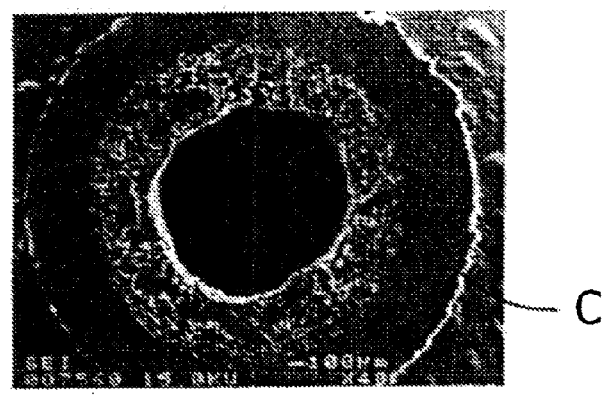
FIG. 4 exhibits a cross-sectional view (×40) of one example of sustained release preparations having an outside of each capillary tube (foamed inner layer) of Examples 1 to 3 covered with a polymer for controlling the penetration rate of a liquid chemical.
Figure 5:
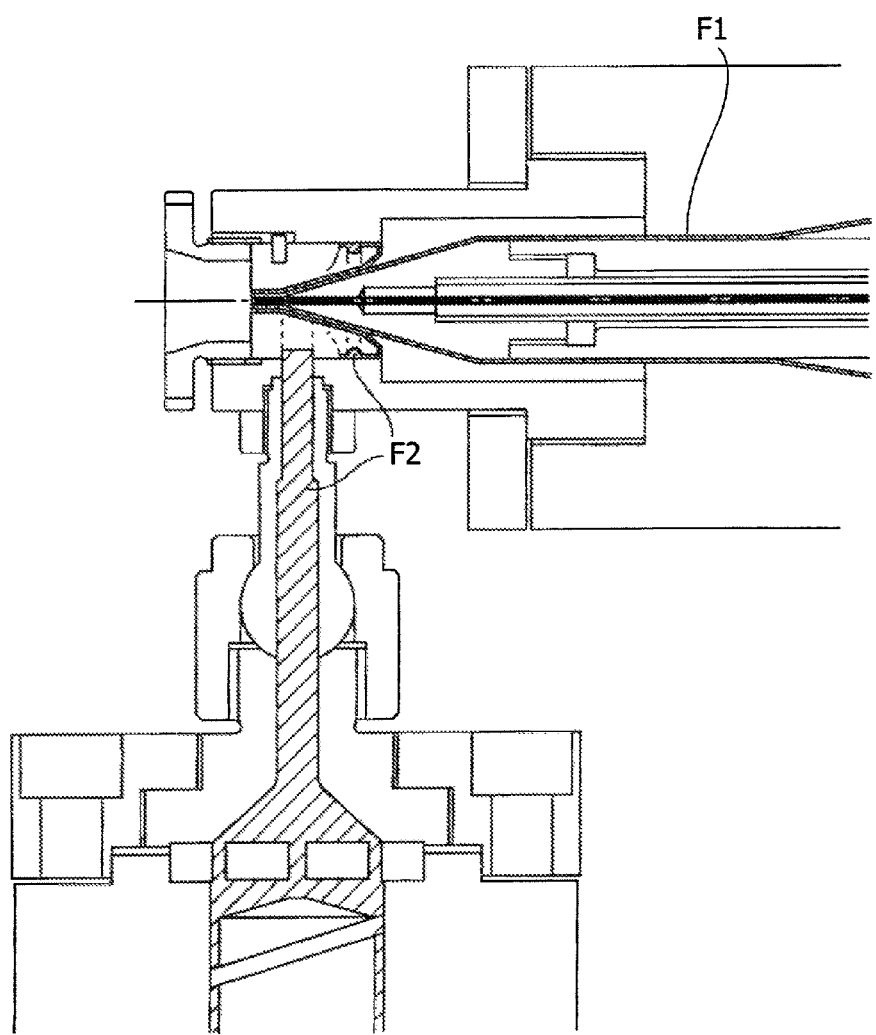
FIG. 5 illustrates an apparatus for producing a container unit for a sustained release preparation.
Figure 6:
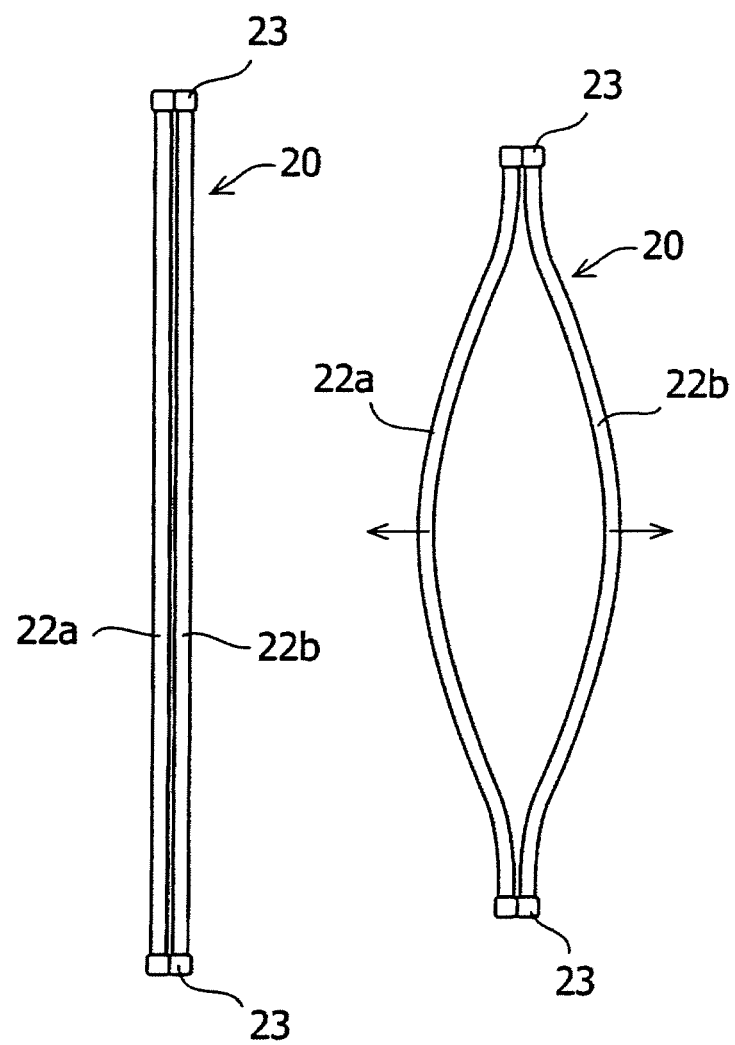
Figure 7:
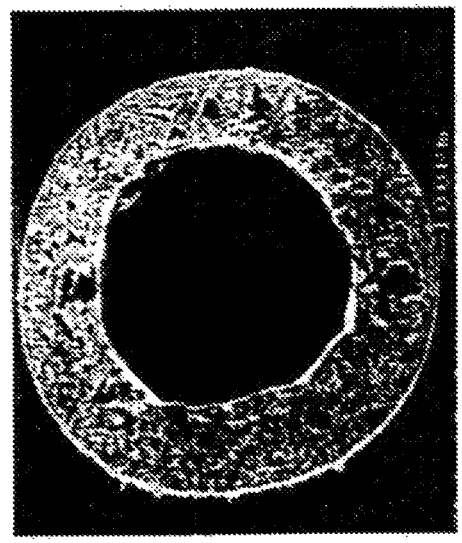
FIG. 7 is a cross-sectional view (×40) illustrating a foamed structure of the inner layer of the sustained release preparation of Example 1.
Figure 8:
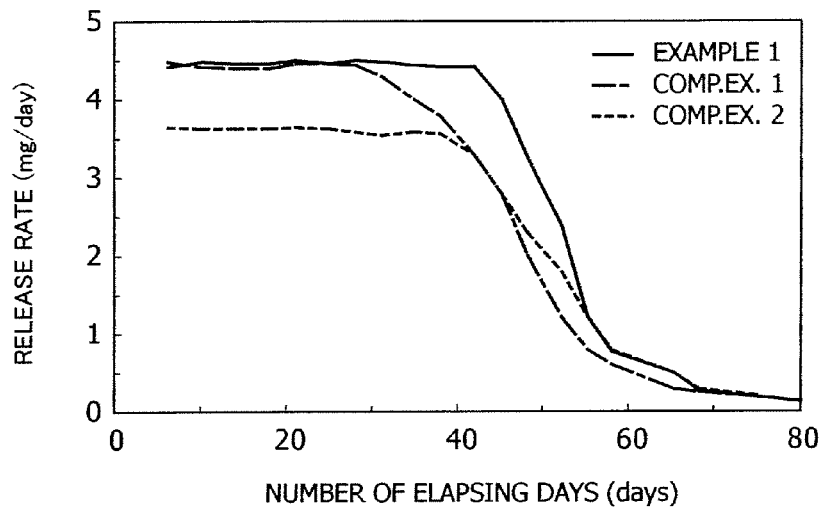
FIG. 8 is a graph showing the correlation between the elapsed time and the amount of sex pheromone of the oriental fruit moth released from sustained release preparations of Example 1, and Comparative Examples 1 and 2.
Figure 9:
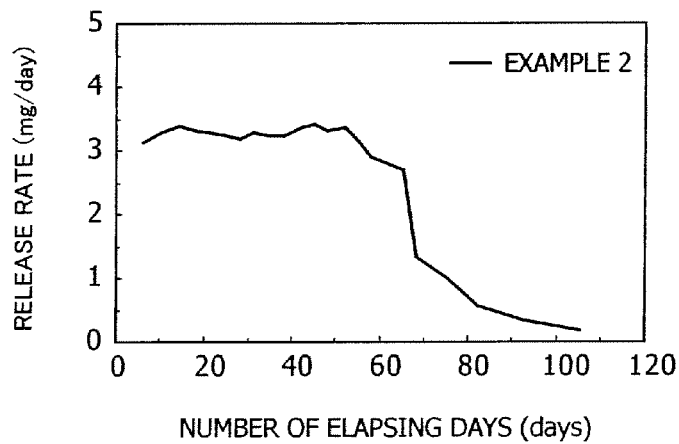
FIG. 9 is a graph showing the correlation between the elapsed time and the amount of sex pheromone of the oriental tea tortrix released from the sustained release preparation of Example 2.
Figure 10:
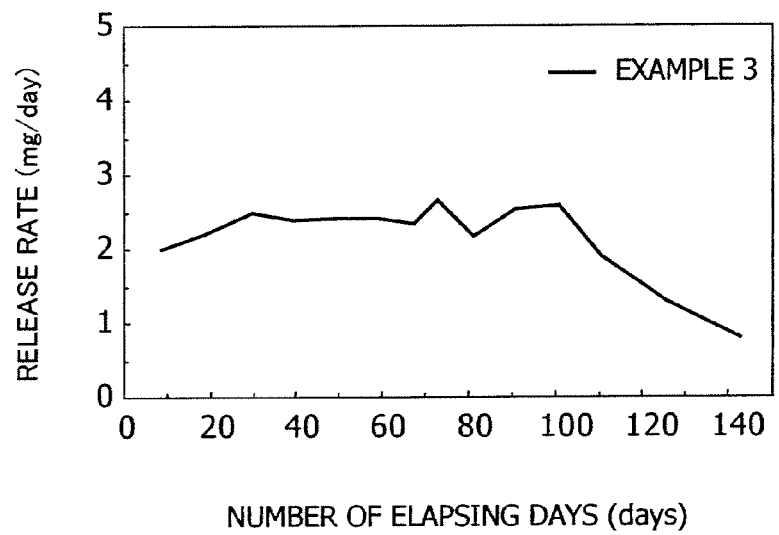
FIG. 10 is a graph showing the correlation between the elapsed time and the amount of a sex pheromone of the peach fruit borer released from the sustained release preparation of Example 3.
Figure 11:
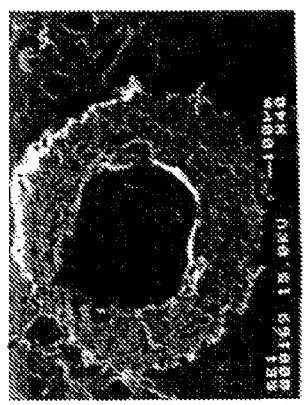
FIG. 11 is a cross-sectional view (×40) showing the foamed structure of the inner layer of the sustained release preparation of Example 4.
Figure 12:
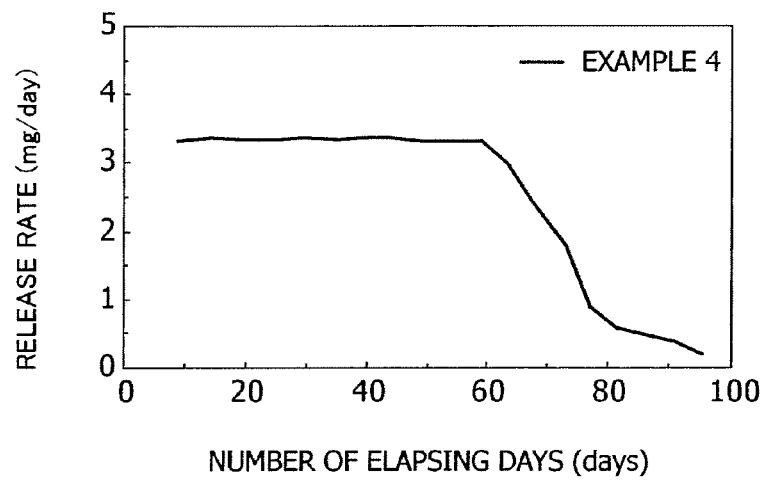
FIG. 12 is a graph showing variations, with time, of the amount of a sex pheromone of the oriental fruit moth released from the sustained release preparation of Example 4.
Figure 13:
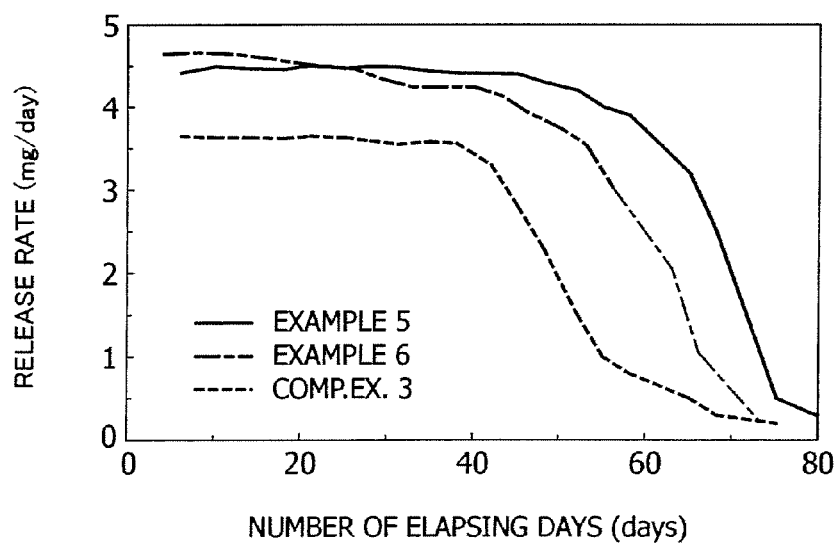
FIG. 13 is a graph showing variations, with time, of the amount of a sex pheromone of the oriental fruit moth released from the sustained release preparations of Example 5, Example 6 and Comparative Example 3.
Figure 14:
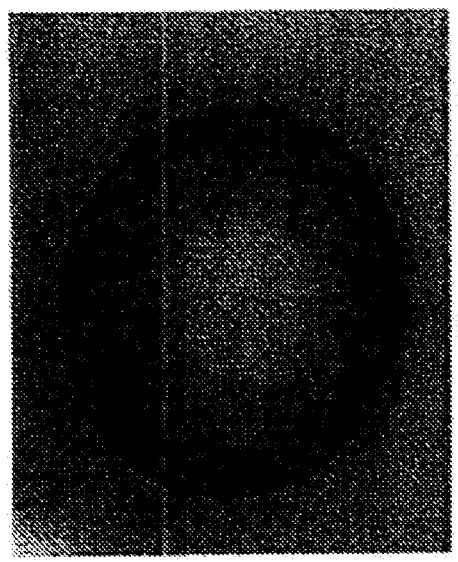
FIG. 14 is a cross-sectional view (×40) showing the foamed structure of the inner layer of the sustained release preparation of Example 7.
Figure 15:
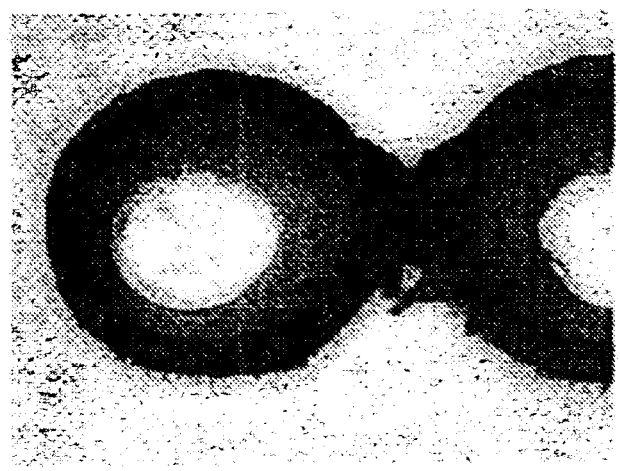
FIG. 15 is a cross-sectional view (×40) showing the foamed structure of the inner layer of the sustained release preparation of Example 8.
Figure 16:
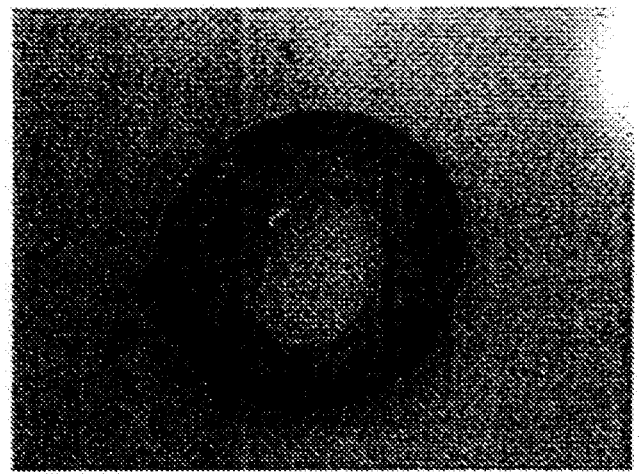
FIG. 16 is a cross-sectional view (×40) showing the foamed structure of the inner layer of the sustained release preparation of Example 9.

11: Capillary tube
12: Liquid chemical
20: Sustained release preparation
22a, 22b: Plastic capillary tubes
23: Fusion connect end
101: Bottle
102: Wire
F1: flow path of inner layer
F2: flow path of outer layer

The invention claimed is:

1. A container for a sustained release preparation, the container being tubular and comprising two layers, an outer and an inner layer, the inner layer having a thickness of 0.12 to 1.2 mm and the inner layer having a foamed structure permitting soaking-up of a liquid chemical to a height exceeding 25 mm by capillarity, wherein the liquid chemical is a sex pheromone, and the foamed structure of the inner layer is formed in a polymer selected from the group consisting of high density polyethylene, low density polyethylene, cross-linked polyethylene, ethylene-vinyl acetate copolymer, aliphatic polyester, blend polymer of polyolefin and aliphatic polyester, and polylactic acid.

2. The container for a sustained release preparation according to claim 1, wherein said inner layer has a cell diameter range of 0.2 to 700 μm.

3. The container for a sustained release preparation according to claim 1, wherein said outer layer comprises a polymer for controlling a penetration rate of said liquid chemical.

4. The container for a sustained release preparation according to claim 3, wherein said polymer for controlling a penetration rate of said liquid chemical is polyolefin, olefin copolymer, aliphatic polyester, or aliphatic ester copolymer.

5. The container for a sustained release preparation according to claim 1, wherein said foamed structure contains said liquid chemical which is a sex pheromone.

6. The container for a sustained release preparation according to claim 1, wherein said inner layer comprises a filler.

7. The container for a sustained release preparation according to claim 1, wherein said inner layer comprises a silica powder.

8. A container unit for a sustained release preparation, the unit comprising two or more containers as claimed in claim 1.

9. A sustained release preparation, comprising the container claimed in claim 1, and a liquid chemical placed in the container.

10. The container for a sustained release preparation according to claim 1, wherein the foamed structure layer has a cell diameter range from 0.2 and 700 μm, and contains from 50 to 95% of cell diameters from 0.2 to 100 μm, and from 5 to 50% of cell diameters from 100-700 μm.

* * * * *